United States Patent [19]

Vinayak

[11] Patent Number: 5,281,701
[45] Date of Patent: Jan. 25, 1994

[54] PROCESS AND COMPOUNDS FOR RNA SYNTHESIS

[75] Inventor: Ravi S. Vinayak, Foster City, Calif.

[73] Assignee: Applied Biosystems, Inc., Foster City, Calif.

[21] Appl. No.: 729,492

[22] Filed: Jul. 12, 1991

[51] Int. Cl.[5] .............. C07H 19/067; C07H 19/167; C07H 21/02

[52] U.S. Cl. .................... 536/25.34; 536/25.31; 536/26.7; 536/26.8; 435/199

[58] Field of Search ............................ 536/27, 28, 29

[56] References Cited

U.S. PATENT DOCUMENTS 4,458,066  7/1984  Caruthers et al. ............ 536/27

OTHER PUBLICATIONS

Vinayak et al./Nucleic Acids Res. 20: 1265–1269 (1992).
Benson/Chem. Rev. 41: 1–61 (1947).
Amarnath et al./Chem. Rev. 77: 183–217 (1977).
Narang/Tetrahedron 39: 3–22 (1983).
Ohtsuka et al./Nucleic Acids Res. 10: 6553–6570 (1982).
Wu et al., Nucleic Acids Research, 17: 3501–3517 (1989).
Schulhof et al., Nucleic Acids Research, 15: 397–416 (1987).
Ogilvie et al., Proc. Natl. Acad. Sci., 85: 5764–5768 (1988).
Wu et al., Tetra. Letters 29: 4249–4252 (1988).
Chaix et al., Tetra. Letters 30: 71–74 (1989).
Vu et al., Tetra. Letters, 31: 7269–7272 (1990).
Scaringe et al., Nucleic Acids Research, 18: 5433–5441 (1990).
Applied biosystems, Inc. User Bulletin No. 53 (Dec. 1, 1989).
MilliGen/Biosearch Technical Note MG-175 (1989).
Glen Research Report 4(1) dated Mar., 1991.
Froehler et al., Nucleic Acids Research, 11: 8031–8036 (1983).
Caruthers, "DNA Synthesis for Non-Chemists: The Phosphoramidite Method on Silica Supports," Chapter 3 in *Synthesis and Applications of DNA and RNA*, Narang ed., Academic Press, Inc., New York, 1987, see particularly pp. 26, 27 and 61–64.
Kaiser et al., Nucleic Acids Research, 17(15), 6087–6102 (1989).
Cai et al., Chem. Abstr., 112, p. 772, Abstr. No. 198,953k (1990).
"RNA Synthesis Reagents," product brochure published by American Bionetics, Hayward, Calif., 1990.

*Primary Examiner*—Johnnie R. Brown
*Assistant Examiner*—L. Eric Crane
*Attorney, Agent, or Firm*—Stephen C. Macevicz

[57] ABSTRACT

A method and compositions are provided for synthesizing polynucleotides wherein the exocyclic amino groups of 5'-O-protected-2'O-alkylsilyl-adenosine phosphoramidite and 5'-O-protected-2'-O-alkylsilylguanosine phosphoramidite monomers are protected with dialkylformamidine. In a preferred embodiment, the ribonucleoside phosphoramidite monomers are activated with ethylthiotetrazole.

12 Claims, 2 Drawing Sheets

PROCESS AND COMPOUNDS FOR RNA SYNTHESIS

FIELD OF THE INVENTION

The invention relates generally to the synthesis of poly- and oligoribonucleotides, and more particularly, to new protected ribonucleoside phosphoramidites and their use in the solid phase synthesis of ribonucleic acid (RNA).

BACKGROUND

The discovery that certain RNAs possess enzymatic activity has led to a search for applications of "ribozymes" ranging from new pharmaceuticals, e.g. Sarver et al., Science, Vol. 247, pp. 1222–1225 (1990), to new tools for molecular biology, e.g. Haseloff et al., Nature, Vol. 334, pp. 585–591 (1988); Cech et al., U.S. Pat. No. 4,987,071; and Ellington et al., Nature, Vol. 346, pp. 818–822 (1990). This increased interest in RNA applications has generated a demand for more effective methods of chemically synthesizing RNA polymers. Unfortunately, progress in the chemical synthesis of RNA has not been as rapid as that for the chemical synthesis of DNA, largely because of the constraints imposed by having to protect the extra hydroxyl attached to the 2' carbon of the ribonucleosides, e.g. Van Boom et al., pp. 153–183, in Gait, ed. *Oligonucleotide Synthesis: A Practical Approach* (IRL Press, Washington, D.C., 1984).

Presently, solid phase approaches provide the most effective means for chemical synthesis of RNA. Such methods proceed by the step-wise addition of protected ribonucleoside phosphoramidite or hydrogen phosphonate monomers to a growing RNA chain attached to a solid phase support, e.g. Scaringe et al., Nucleic Acids Research, Vol. 18, pp. 5433–5441 (1990); Wu et al., Tetrahedron Letters, Vol. 29, pp. 4249–4252 (1988); Wu et al., Nucleic Acids Research, Vol. 17, pp. 3501–3517 (1989); Stawinski et al., Nucleic Acids Research, Vol. 16, pp. 9285–9298 (1988). An important advance in solid phase RNA synthesis came with the introduction of alkylsilyl protection groups, e.g. t-butyldimethylsilyl(TBDMS), for the 2'-hydroxyl position, e.g. Ogilvie et al., Can. J. Chem., Vol 57, pp. 2230–2238 (1979). Difficulties still remains, however, because of the lability of the alkylsilyl groups under commonly used base deprotection conditions. Base protection groups, such as benzoyl, isobutyryl, and the like, are removed under relatively harsh basic conditions, e.g. 3:1 ammonium hydroxide-ethanol for 18 h at 55° C. that can lead to the removal of a small but significant fraction of alkylsilyl protection groups, e.g. Wu et al. Nucleic Acids Research (cited above). With the 2'-hydroxyl unprotected, a small but significant fraction of the freshly synthesized RNA chains will be cleaved, resulting in a drop in yield of full length chains. If milder base deprotection conditions are employed, deprotection could be incomplete resulting in a drop in yield of biologically active material because of the interfering base protection groups remaining on the RNA chain.

SUMMARY OF THE INVENTION

The present invention is directed to a method and compositions for RNA synthesis. The compositions include protected adenosine and guanosine phosphoramidite monomers for use in the method. Important features of the invention include the protection of the exocyclic amino groups of adenosine and guanosine, or like analogs, with dialkylformamidine (DMF) and the activation of the nucleoside phosphoramidites with ethylthiotetrazole (ETT) during the addition step of the synthesis cycle. The DMF protection groups are removed much more rapidly under standard basic conditions than currently used exocyclic amino protection groups. It is believed that reduced exposure of the 2'-alkylsilyl protection groups to the based conditions prevents premature deprotection of the 2'-hydroxyl and subsequent chain cleavage. Ethylthiotetrazole leads to more rapid and complete monomer addition during the synthesis cycle.

Preferably, the protected ribonucleoside phospharamidites for use in the method of the invention are selected from the group defined by the following formulas:

Formula 1

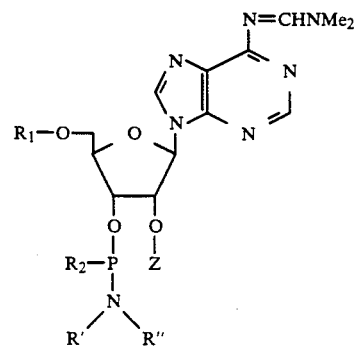

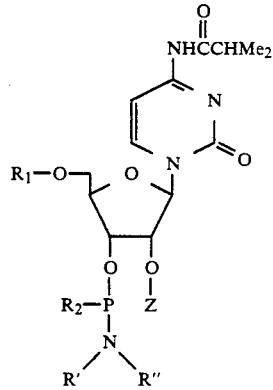

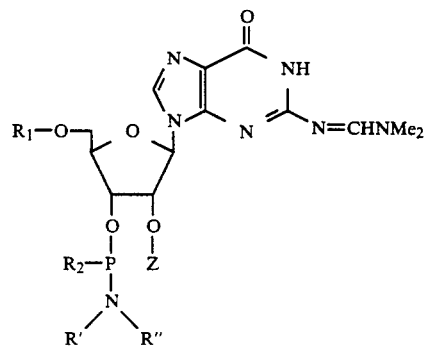

-continued
Formula 1

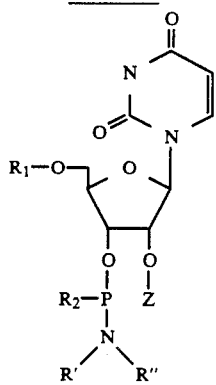

wherein:

$R_1$ is a 5'-hydroxyl protection group, e.g. Atkinson et al., pp. 35–81 in Gait, ed. *Oligonucleotide Synthesis: A Practical Approach* (IRL Press, Washington, D.C. 1984); or Amarnath et al., Chemical Reviews, Vol. 77, pp. 183–217 (1977). Preferably, $R_1$ is trityl; more preferably, $R_1$ is monomethoxytrityl or dimethoxytrityl; and most preferably, $R_1$ is dimethoxytrityl.

$R_2$ is a phosphate protection group. Preferably, $R_2$ is lower alkyl; electron-withdrawing $\beta$-substituted ethyl, particularly $\beta$-trihalomethyl-, $\beta$-cyano-, $\beta$-sulfo-, $\beta$-nitro- substituted ethyl, or the like; electron-withdrawing substituted phenyl, particularly halo-, sulfo-, cyano-, nitro-, substituted phenyl; or electron-withdrawing substituted phenylethyl. More preferably, $R_2$ is methyl, $\beta$-cyanoethyl, or 4-nitrophenylethyl; and most preferably, $R_2$ is $\beta$-cyanoethyl.

$R'$ and $R''$ taken separately each represent alkyl, aralkyl, cycloalkyl, and cycloalkylalkyl containing up to 10 carbon atoms. Preferably $R'$ and $R''$ taken separately represent lower alkyl; and more preferably, $R'$ and $R''$ taken separately are sterically hindering lower alkyls which enhance the chemical stability of the phosphoramidites, and hence their shelf lives. Such sterically hindering lower alkyls include isopropyl, t-butyl, isobutyl, sec-butyl, neopentyl, tert-pentyl, isopentyl, sec-pentyl, and the like. Most preferably, $R'$ and $R''$ taken separately are isopropyl. $R'$ and $R''$ taken together form an alkylene chain containing up to 5 carbon atoms in the principal chain and a total of up to 10 carbon atoms with both terminal valence bonds of said chain being attached to the nitrogen atom to which $R'$ and $R''$ are attached; or $R'$ and $R''$ when taken together with the nitrogen atom to which they are attached form a saturated nitrogen heterocycle which may contain one or more additional heteroatoms from the group consisting of nitrogen, oxygen, and sulfur. More preferably, $R'$ and $R''$ taken together and with the nitrogen to which they are attached are pyrrolidino, morpholino, or piperidino. Most preferably, $R'$ and $R''$ taken together and with the nitrogen to which they are attached are morpholino.

Z is a 2'-hydroxyl protection group. Preferably, Z is of the form $SiE_1E_2E_3$, wherein $E_1$, $E_2$, and $E_3$ are sterically hindering lower alkyls. More preferably, Z is t-butyldimethylsilyl (TBDMS) or triisopropylsilyl; and most preferably, Z is TBDMS.

As used herein, the term lower alkyl refers to straight-chained, branched, or cyclic alkyls containing from 1 to 6 carbon atoms, e.g. methyl, ethyl, propyl, isopropyl, tert-butyl, isobutyl, sec-butyl, neopentyl, tert-pentyl, and the like. "Lower substituted alkyl" denotes lower alkyl having electron-withdrawing substituents, such as halo, cyano, nitro, sulfo, or mono-, di-, or trihalomethyl, or the like. "Lower haloalkyl" denotes a lower alkyl with one or more halogen atom substituents, usually fluoro, chloro, bromo, or iodo.

The term "polyribonucleotide" as used herein includes linear polymers of natural or modified ribonucleosides linked by phosphodiester bonds or analogs thereof ranging in size from a few monomeric units, e.g. 2–3, to several hundred monomeric units. In particular, the term includes non-natural oligomers having phosphorous-containing linkages whose phosphorous(III) precursors are amenable to sulfurization, e.g. Takeshita et al., J. Biol. Chem., vol. 282, pp. 10171–10179 (1987); and Eapienis et al., pp. 225–230 in, Bruzik and Stec, eds., *Biophosphates and Their Analogs-Synthesis, Structure, Metabolism, and Activity* (Elsevier, Amsterdam, 1986).

"Electron-withdrawing" denotes the tendency of a substituent to attract valence electrons of the molecule of which is is apart, i.e. it is electronegative, March, *Advanced Organic Chemistry*, pp. 16–18 (John Wiley, New York, 1985).

DETAILED DESCRIPTION OF THE INVENTION

Figure 1A:
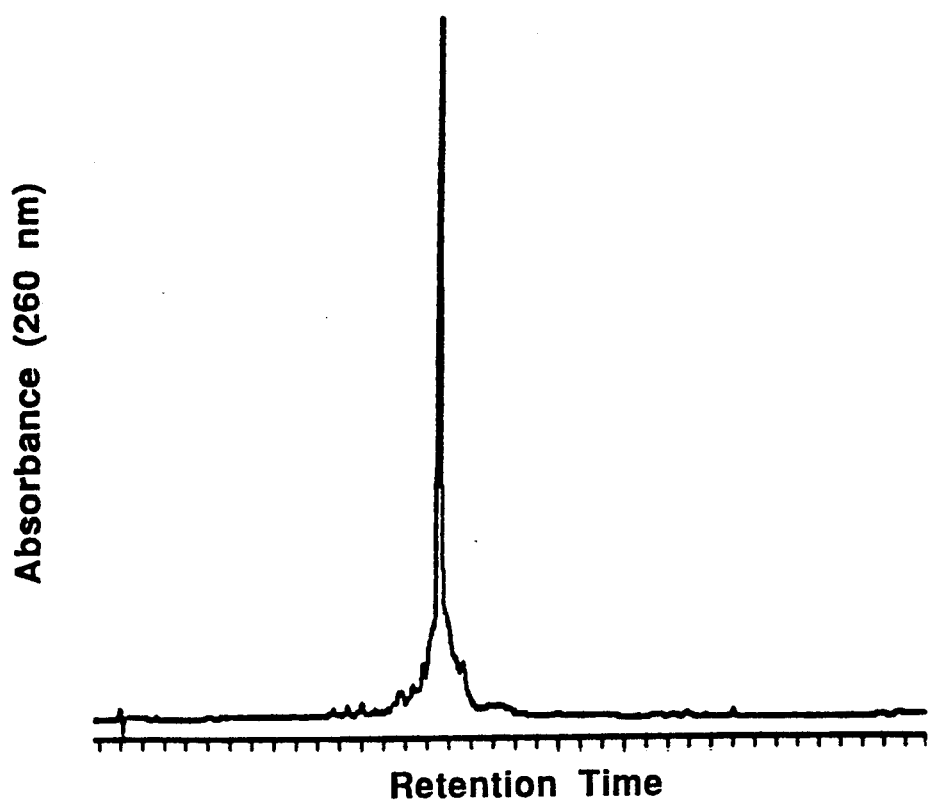
FIGS. 1A and 1B are chromatograms of RNA products synthesized with an automated DNA synthesizer with monomers of the invention (A) and with benzoyl-protected monomers (B) on a uridine support.

The invention relates to a method of solid phase synthesis of polyribonucleotides using ribonucleoside phosphoramidite monomers selected from the set defined in Formula 1. The invention also includes the use of ethylthiotetrazole as an activating agent during the coupling step of the synthesis cycle.

Generally, synthesis of polyribonucleosides in accordance with the invention follows the phosphoramidite approach to solid phase nucleotide synthesis, which is described in the following references, which are incorporated by reference: Caruthers et al., U.S. Pat. Nos. 4,458,066 and 4,500,707; Koester et al., U.S. Pat. No. 4,725,677 Matteucci et al., *J. Amer. Chem. Soc.*, Vol. 103, pp. 3185–3191 (1981); Caruthers et al., *Genetic Engineering*, Vol. 4, pp. 1–17 (1981); Caruthers et al., Meth. Enzymol., Vol. 154, pp. 287–313 (1987); Jones, chapter 2, and Atkinson et al., chapter 3, in Gait, ed., *Oligonucleotide Synthesis: A Practical Approach* (IRL Press, Washington, D.C., 1984); and Brill et al., J. Am. Chem. Soc., Vol. 111, p. 2321 (1989).

Preferably, adenosine and guanosine monomers of the invention are prepared from the unprotected ribonucleoside by the following steps: i) protecting the exocyclic amino group on the base moiety DMF; ii) protecting the 5'-hydroxyl; iii) protecting the 2'-hydroxyl; and iv) adding the protected phosphoramidite moiety to the 3'-hydroxyl.

2-N-Dimethylformamidine-guanosine is prepared by reacting guanosine with N,N-dimethylformamide dimethyl acetal in methanol, formamide, or like solvent, to form $G^{dmf}$ following the procedure described in Zemlicka, Collect. Czech. Chem. Commun., Vol. 28, p. 1060 (1962); Holy et al., Collect. Czech. Chem. Commun., Vol. 34, p. 2449 (1969); and Hostomski et al., Collect Czech. Chem. Commun., Vol. 54, p. 523 (1989), which are incorporated by reference, 2-N-Dialkylformamidine-guanosine is prepared similarly by substituting the appropriate N,N-dialkylformamidine dimethyl acetal in the above reaction. Dialkylformamide dimethyl acetals may be purchased commercially, or synthesized in accordance with Froeler et al., Nuclear Acids Research, Vol 11, pp. 8031–8036 (1983); Brederech et al., Chem. Ber., Vol. 101, p. 41 (1968); or the like. Preferably, the 5'-hydroxyl of the $G^{dmf}$ product is protected by tritylation, e.g. by reacting with 4,4'-dimethoxytrityl chloride in pyridine using standard procedures, e.g. Caruthers et al., U.S. Pat. No. 4,973,679, to form DMT-$G^{dmf}$.

The DMT-$G^{dmf}$ product is silylated by standard procedures, e.g. as described by Hakimelahi et al., Can. J. Chem., Vol. 60, pp. 1106–1113 (1982); Usman et al., J. Am. Chem. Soc., Vol. 109, pp. 7845–7854 (1987); Pon et al., Nucleic Acids Research, Vol. 14, pp. 6453–6470 (1986); or the like. The 2'-O-silylated products are separated from the 3'-O-silylated products by silica gel chromatography in accordance with Hakimelahi et al., (cited above). The purified 2'-O-silylated product is then phosphitylated by standard procedures, e.g. Barone et al., Nucleic Acids Research, Vol. 12, pp. 4051–4061 (1984); Scaringe et al. (cited above); Koster et al., U.S. Pat. No. 4,725,677; or the like. Briefly, the 2'-O-silylated product is reacted with a halo-substituted-N,N-di-substituted-O-substituted phosphine defined by the formula:

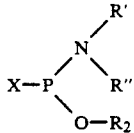

wherein X is a halogen, usually chloro, and R', R", and $R_2$ are as indicated above, in an aprotic solvent, such as dichloromethane, or the like, containing a non-nucleophilic base, for example a trialkylamine, such as N,N-diisopropylamine, or the like, which absorbs the halogen acid released during the reaction. The DMT-$G^{dmf}$ phosphoramidite is purified by silica gel chromatography using 40–60 micron particles and 9:1 (v/v) ethylacetate-triethylamine as eluant.

6-N-dimethylformamidine-5'-O-DMT-2'-O-alkylsilyl-adenosine-3'-O-phosphoramidite is prepared by similar procedures. 4-N-isobutyryl-5'-O-DMT-2'-O-alkylsilyl-cytidine is prepared as described by Schulhof et al., Nucleic Acids Research, Vol. 15, 397–416 (1987), which is incorporated by reference.

Preferably, the method of the invention is implemented on a commercially available automated DNA synthesizer, e.g. an Applied Biosystems, Inc. (Foster City, Calif.) model 380B, of like instrument. Generally, the synthesis consists of a series of addition cycles comprising the following steps: (1) deprotecting a blocked hydroxyl (usually a 5'-tritylated hydroxyl) on a growing correct-sequence chain, or on an initial monomer attached to a solid phase support, to form a free hydroxyl, (2) coupling a protected ribonucleoside phosphoramidite or phosphorthioamidite monomer or analog thereof in the presence of an activator, e.g. tetrazole or ETT, with the free hydroxyl of the growing correct-sequence chain, (3) capping unreacted hydroxyls, (4) oxidizing the newly formed phosphorous(III) linkage to form the naturally occurring pentacoordinate state (The sequence of steps (3) and (4) can be reversed), and (5) repeating the steps until desired polyribonucleotide chain is obtained. After the synthesis is completed, the polyribonucleotides are cleaved from the support and the exocyclic amino groups are deprotected simultaneously by treatment with base, preferably 3:1 ammonium hydroxide:ethanol for 1–2 h at 55°–60° C. After separating the polyribonucleotides from the solid phase support material and deprotection reagents (e.g. by centrifugation, decanting the supernatant, evaporation), the alkylsilyl protection groups are removed by standard procedures, e.g. treatment with 1M tetrabutylammonium fluoride in tetrahydrofuran. Finally, the completely deprotected polyribonucleotide is detritylated and separated from failure sequences, e.g. by means of a commercially available ion exchange cartridges, such as Applied Biosystems, Inc. OPC, McBride et al., BioTechniques, Vol. 6, pp. 362–367 (1988), or the like.

Preferably, ethylthiotetrazole (ETT) is used to activate the phosphoramidite during the coupling step. Preferably, ETT is used at a concentration in the range of 0.4 to 0.6 molar; more preferably, it is used at a concentration of 0.5–0.6 molar. ETT can be made by the following procedure: In a 1 liter round-bottom flask with internal thermometer at room temperature. 20.0 ml ethylthiocyanate is added, followed by 150–300 ml of dimethylformamide (DMF). Ammonium chloride (18.75 gm), then sodium azide (22.79 gm) are added as solids. The flask is fitted with a condenser (no cooling water required) and a nitrogen inlet at the top. The temperature is raised to 95°–100° C. with either an oil bath or heating mantle and the mixture is magnetically stirred. After 18 hours, the flask is fitted with a distillation head, condenser, and receiver flask. The receiver flask is cooled by ice. The mixture is subjected to water aspirator vacuum. Any unreacted ethylthiocyanate nd most of the DMF is distilled this way. The stirring bas is removed and the remainder of the volatile compounds are removed under vacuum on a rotary evaporator with a vacuum pump (1–5) mm Hg). Distilled water (100 ml) is added and again evaporated on the rotary evaporator to dryness. The flask is transferred to a fume hood and 300 ml distilled water is added with swirling. Enough 10% hydrochloric acid (about 10 ml) is added to make the solution acidic (pH=1–2). (Caution: hydrazoic acid is generated form the excess sodium azide). A heavy white precipitate immediately forms from the cream-colored solution. The flask is stoppered and allowed to stand in a refrigerator or on ice for at least several hours. The product is filtered, washing with 200 ml cold water. The filter funnel containing the product is dried in a vacuum disicator for at least several hours. The product can be assessed by TLC ($R_f$=0.4, $CH_2Cl_2$:$CH_3OH$:$CH_3CO_2H$/20:1:1). Dissolution in a minimum amount of ethyl acetate (about 200 ml) with heating is followed by filtration into a 500 ml round-bottom flask, washing the funnel and flask with ethyl acetate. The mother liquor is concentrated by about one half on a rotary evaporator and then heated again with a heat gun to a solution or near solution. Hexane (about 200 ml) is added slowly to maintain precipitation of loose crystals. The flask is then stoppered and stored in a refrigerator or on ice for at least several hours. The product is filtered, washing with 100 ml ethyl acetate:hexane/1:1 and dried under vacuum. Several grams of product may be removed from the mother liquor is desired by concentration and crystallization. The white dense crystals have a melting point of 147°–149° C. and a molecular weight of 116.1. About a 70% yield can be expected.

EXAMPLES

Example 1

Synthesis of 2'-O-(t-butyldimethylsilyl)-5'-O-4,4-(dimethoxytrityl)-2-N-dimethylformamidine guanosine A suspension of guanosine (10 mmoles) in N,N-dimethylformamide (25 ml) and N,N-dimethylformamidediethylacetal (6 ml) is stirred overnight. To the clear solution, water (1 ml) is added. After 5 minutes the solution is diluted with pyridine (100 ml) and the mixture evaporated to a syrup. Pyridine (30 ml) and 4,4'-dimethoxytritylchloride (11 mmoles) are added, the mixture stirred 10 minutes, and tert-butyldimethylchlorosilane (13 mmoles) added. Stirring continues for 1 hour. The mixture is partitioned between chloroform (60 ml) and water (30 ml). Water layer is extracted with chloroform (10 ml) and the combined chloroform extracts are diluted with toluene (30 ml) and evaporated. The residue is dissolved in toluene and evaporated under vacuum. The resulting foam is dissolved in chloroform (20 ml) containing triethylamine (0.5% v/v) and applied on a silica gel column (400 ml) equilibrated in the same solvent. Elution is performed by a series of 250 ml portions of 995:50 chloroform:triethylamine containing in sequence, 0, 1,2,3, 5, and 6 percent 2-propanol. After the eluate became positive, fractions of 50 ml are collected and checked by TLC in 9:1 chloroform:2-propanol. Fractions 12–17 contain the pure 2'-O-TBDMS isomer, and after evaporation and coevaporation with chloroform yield 5.1 g of product.

Example 2

Synthesis of 2'-O-(t-butyldimethylsily)-5'-O-4,4-(dimethoxytrityl)-2-N-dimethylformamidine adenosine The compound is prepared from adenosine (10 mmoles) by the same procedure as in Example 1, except that in purification subsequent 250 ml portions of 995:50 chloroform:triethylamine contained 0.25, 0.5, 0.75, 1.0, 1.25, and 1.25 percent of 2-propanol.

Example 3

Phosphitylation of protected ribonucleoside monomers

Cyanoethyl diisopropyl phosphoramidites of the protected ribonucleoside monomers is synthesized by standard procedures with minor modifications, e.g. Sinha et al., Nucleic Acids Research, Vol. 12, pp. 4539–4557 (1984); and Kaiser et al., Nucleic Acids Research, Vol. 17, pp. 6087–6103 (1989). The monomer alcohol (1,5 mmoles) is suspended in dry dichloromethane (20 ml, HPLC grade dried by passage over basic alumina) under argon, and dry N,N-diisopropylethylamine (4.5 mmoles, dried by refluxing over and distillation from calcium hydride) is added, followed immediately by 2-cyanoethyl-N,N-diisopropylchlorophosphoramidite (3.0 mmoles). The solid rapidly dissolves to give a clear solution. The reaction is stirred 15 minutes at room temperature, and is diluted with ethyl acetate (100 ml, previously washed with ice cold 5% w/v aqueous sodium bicarbonate (2×50 ml) and with cold saturated aqueous sodium chloride (50 ml). It is dried over anhydrous sodium sulfate, filtered, and evaporated to a pale yellow oil under reduced pressure (water aspirator) below 35° C. The crude product is dried overnight in vacuo over KOH pellets. The product is purified by flash chromatography on a silica gel using 60:35:5 hexane:ethyl acetate:pyridine as the eluant, e.g. Still et al., J. Org. Chem., Vol. 43, pp. 2923–2925 (1978).

Example 4

Comparison of 18-mer polyribonucleotide product synthesized with benzoyl-protected adenosine, cytidine, and guanosine monomers with polyribonucleotide product synthesized with DMF-protected adenosine and quanosine monomers and isobutyryl-protected cytidine monomers Two pairs of polyribonucleotide sequences, 5'-UCA CAG UCU GAU CUC GAU-3' and 5'-UCA CAG UCU GAU CUC GAG-3', were synthesized. One pair (pair 1) was synthesized from the following monomers of the invention: 2'-O-(t-butyldimethylsilyl) -5'-O-4,4-(dimthoxyrityl)-2-N-dimethylformamidine adenosine-3'-cyanoethyldiisopropylphosphoramidite; 2'-O(t-butyldimethylsilyl) -5'-O-4,4-(dimethoxytrityl)-2-N-dimethylformamidine guanosine-3'-cyanoethyldiisopropylphosphoramidite; 4-N-isobutyryl-5'-O-DMT-2'-O-alkylsilyl-cytidine-3'-cyanoethyldiisopropylphosphoramidite; and 2'-O-(t-butyldimethylsilyl)-5'-O-4,4-(dimethoxytrityl)-uridine-3'-cyanoethyldiisopropylphosphoramidite. The other pair of polynucleotides (pair 2) was synthesized with uridine and benzoyl-protected adenosine, guanosine, and cytidine cyanoethyldiisopropylphosphoramidite monomers (available commercially from Milligen/Biosearch, Burlington, Mass). All syntheses were carried out on an Applied Biosystems, Inc. model 380B DNA synthesizer on a 1.0 micromole scale using derivatized 1000 Angstrom controlled-pore glass solid phase supports (available from the manufacturer). Pair 1 was synthesized in accordance with manufacturer's protocol (ABI User Bulletin No. 53 Dec. 1, 1989) and pair 2 was synthesized in accordance with MilliGen/Biosearch Technical Note MG-175, with the following exceptions: In the synthesis of pair 1, (i) a 0.4 molar solution of ETT was employed in coupling steps of 3–4 minutes, and (ii) deprotection of the DMF protection groups was achieved by treatment in 3:1 ammonium hydroxide:ethanol at 55° C. for 1 hour. In all cases the crude deprotected product cleaved from the synthesis support was de-salted and partially purified prior to HPLC analysis on a commercially available ion exchange cartridge, e.g. Applied Biosystems, Inc. OPC (trityl groups cleave during this step).

Figure 1B:
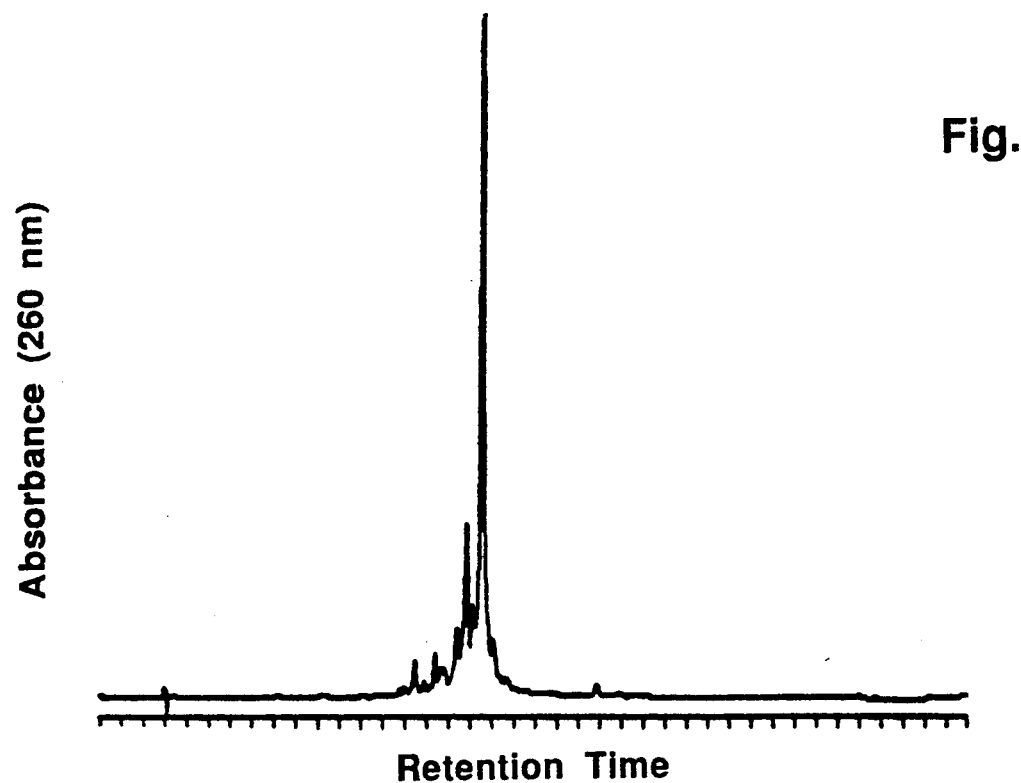
Figure 2A:
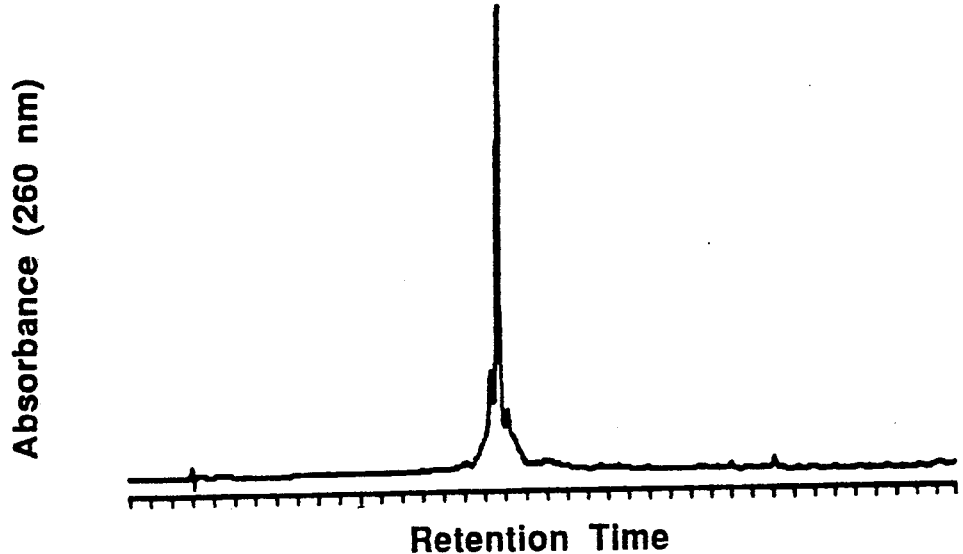
FIGS. 2A and 2B are chromatograms of RNA products synthesized with an automated DNA synthesizer with monomers of the invention (A) and with benzoyl-protected monomers (B) on a guanosine support.
Figure 2B:
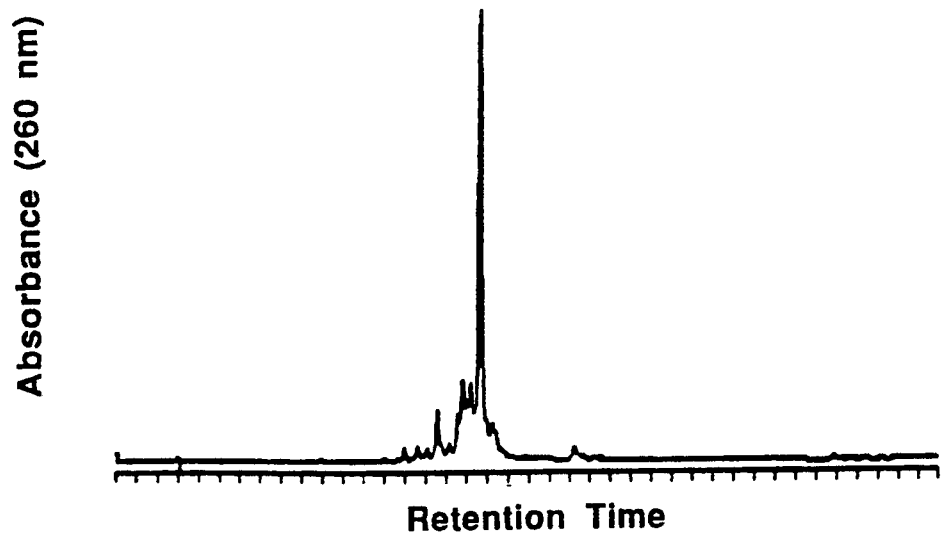

Samples from all OPC-purified products were analyzed by HPLC (Applied Biosystems model 152A with RP300 Brownlee column) with an triethylammonium acetate:acetonitrile gradient going from 0% to 20% in 24 minutes and from 20% to 40% in 34 minutes. FIGS. 1 and 2 illustrate absorption at 260 nm. In both cases, the samples made with the monomers of the invention contain significantly less degraded product.

We claim:

1. A compound selected from the group defined by the following formula:

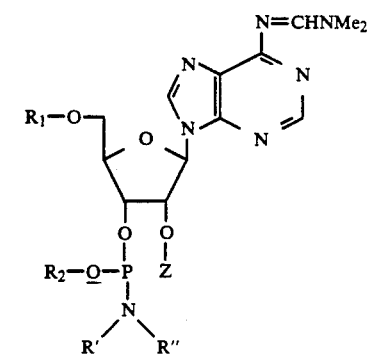

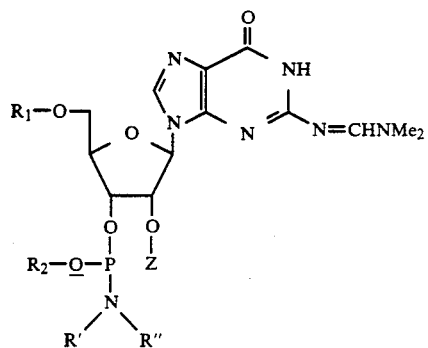

wherein:
R₁ is a 5'-hydroxyl protection group;
R₂ is a phosphate protection group;
R' and R" taken separately are each alkyl, aralkyl, cycloalkyl, and cycloalkylalkyl containing up to 10 carbon atoms, and R' and R" taken together form an alkylene chain containing up to 5 carbon atoms in the principal chain and a total of up to 10 carbon atoms with both terminal valence bonds of said chain being attached to the nitrogen atom to which R' and R" are attached, or R' and R" when taken together with the nitrogen atom to which they are attached are pyrrolidino, morpholino, or piperidino; and
Z is selected from the group consisting of t-butyldimethylsilyl and triisopropylsilyl.

2. The compound of claim 1 wherein R' and R" taken separately are each lower alkyl having from 1 to 6 carbon atoms, and R' and R" taken together and with the nitrogen to which they are attached are pyrrolidino, morpholino, or piperidino.

3. The compound of claim 2 wherein R' and R" taken separately are each isopropyl, and R' and R" taken together with the nitrogen to which they are attached are morpholino.

4. The compound of claim 3 wherein:
R₁ is monomethoxytrityl or dimethoxytrityl;
R₂ is B-cyanoethyl; and
Z is t-butyldimethylsilyl.

5. In a process for synthesizing a polyribonucleotide of a predetermined sequence having at least one non-uridine ribonucleoside, the method of the type wherein protected ribonucleoside phosphoramidite monomers are added stepwise to a growing polyribonucleotide chain attached to a solid phase support and wherein the phosphoramidite moiety of the monomer is activated during a coupling step, an improvement comprising:
providing a protected ribonucleoside phosphoramidite selected from the group defined by the following formula:

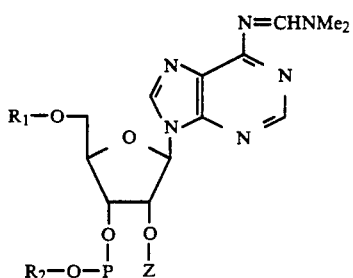

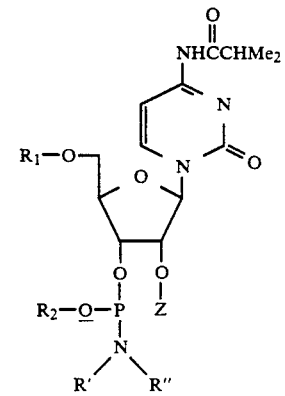

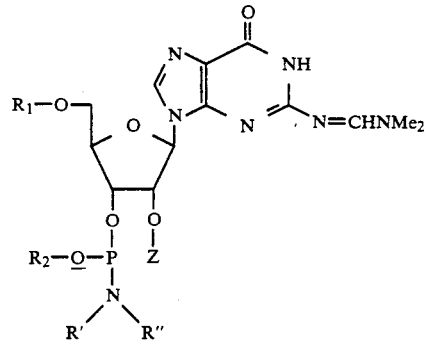

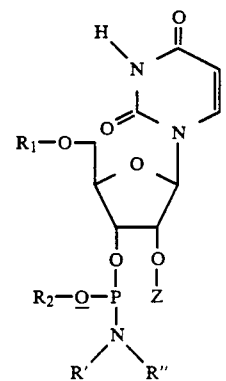

wherein:
R₁ is a t'-hydroxyl protection group;

$R_2$ is a phosphate protection group;

R' and R" taken separately are each alkyl, aralkyl, cycloalkyl, and cycloalkylalkyl containing up to 10 carbon atoms, and R' and R" taken together form an alkylene chain containing up to 5 carbon atoms in the principal chain and a total of up to 10 carbon atoms with both terminal valence bonds of said chain being attached to the nitrogen atom to which R' and R" are attached, or R' and R" when taken together with the nitrogen atom to which they are attached are pyrrolidino, morpholino, or piperidino; and Z is selected from the group consisting of t-butyldimethylsilyl and triisopropylsilyl.

6. The process of claim 5 wherein:

$R_1$ is trityl;

$R_2$ is selected from the group consisting of lower alkyl having from 1 to 6 carbon atoms; β-trihalomethyl-, β-cyano-, β-sulfo-, β-nitro- substituted ethyl; halo-, sulfo-, cyano-, or nitro-substituted phenyl; and electron-withdrawing substituted phenylethyl; and;

R' and R" taken separately are each lower alkyl having from 1 to 6 carbon atoms, and R' and R" taken together and with the nitrogen to which they are attached are pyrrolidino, morpholino, or piperidino.

7. The process of claim 6 wherein $R_1$ is monomethoxytrityl or dimethoxytrityl.

8. The process of claim 7 wherein:

$R_1$ is dimethoxytrityl;

$R_2$ is β-cyanoethyl;

R' and R" taken separately are each isopropyl, and R' and R" taken together and with the nitrogen to which they are attached are morpholino; and Z is t-butyldimethylsilyl.

9. In a process for synthesizing a polyribonucleotide of a predetermined sequence, the method of the type wherein protected ribonucleoside phosphoramidite monomers are reacted with a free hydroxyl of a growing polyribonucleotide chain attached to a solid phase support in the presence of a phosphoramidite activating agent, an improvement comprising reacting the protected ribonucleoside phosphoramidite monomer to a free hydroxyl of a growing polyribonucleotide chain in the presence of a phosphoramidite activating agent consisting of ethylthiotetrazole.

10. The process of claim 9 wherein said ethylthiotetrazole is present in a concentration between 0.4 and 0.6 molar.

11. The process of claim 7 wherein said improvement further includes the step of activating said phosphoramidite moiety of said monomer by ethylthiotetrazole.

12. The process of claim 11 wherein said step of activating includes exposing said phosphoramidite moiety of said monomer to a 0.4 to 0.6 molar solution of ethylthiotetrazole.

* * * * *